(12) United States Patent
Fernandez-Valle et al.

(10) Patent No.: US 9,226,920 B1
(45) Date of Patent: Jan. 5, 2016

(54) METHODS OF INDUCING AND PREVENTING NEUROFIBROMATOSIS IN SCHWANN CELLS

(75) Inventors: Cristina Fernandez-Valle, Oviedo, FL (US); Courtney Thaxton, Orlando, FL (US); Jorge Lopera, Orlando, FL (US); Marga Bott, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 1611 days.

(21) Appl. No.: 12/137,795

(22) Filed: Jun. 12, 2008

Related U.S. Application Data

(60) Provisional application No. 60/946,782, filed on Jun. 28, 2007, provisional application No. 60/955,141, filed on Aug. 10, 2007.

(51) Int. Cl.
*A61K 31/428* (2006.01)
*C07C 255/40* (2006.01)
*A61K 31/43* (2006.01)

(52) U.S. Cl.
CPC ..................................... *A61K 31/43* (2013.01)

(58) Field of Classification Search
CPC ..... A61K 31/015; A61K 31/05; A61K 31/10; A61K 31/135; A61K 31/381; A61K 31/428; C07C 39/08; C07C 39/23; C07C 2102/08; C07C 215/28; C07C 215/70; C07C 221/00; C07C 225/18; C07C 255/07; C07C 255/36; C07C 255/40
See application file for complete search history.

(56) References Cited

PUBLICATIONS

Rong, R., et al, Oncogene, 23: 8447-8454, 2004.*
Obremski, V., J., et al. J. Nerobiol. 37: 487-501, 1998.*
Frohnert, P.W. et al., Glia, 43: 104-118, 2003.*
Stonecypher, M.S., et al., Oncogene, 24: 5589-5605, 2005.*
Fernandez-Valle, C., et al, Journal of Neurobiology, 25(10, 12-7-1226, 1994, abstract only.*
Murillo, H. et al, Cancer Research, 61: 7408-7412, 2001.*
Bowers, G., et al, Oncogene, 20: 1388-1397, 2001.*
Fernandez, A., et al, Int. J. Cancer 83: 564-570, 1999.*

* cited by examiner

*Primary Examiner* — Misook Yu
*Assistant Examiner* — Anne Holleran
(74) *Attorney, Agent, or Firm* — Timothy H. Van Dyke; Beusse, Wolter, Sanks & Maire, PLLC

(57) ABSTRACT

The invention provides a method of inducing neurofibromatosis type 2 (NF2) in Schwann cells. The method comprises contacting the cells with laminin-1 so as to bind α6β1 integrin sufficiently to activate endogenous kinase Cdc42-Pak; and phosphorylating Schwannomin-S518 in the cells by the activated kinase, effectively inactivating Schwannomin's tumor suppressor activity and allowing proliferation of subconfluent Schwann cells, thereby modeling NF2. The invention also includes a method of preventing a Schwann cell from forming a tumor by contacting the cell with an amount of tyrphostin AG825 sufficient to inhibit a receptor selected from ErB2, ErB3, β1 integrins and combinations thereof, so as to prevent phosphorylation of Schwannomin-S815 by one or more endogenous kinases.

2 Claims, 8 Drawing Sheets

METHODS OF INDUCING AND PREVENTING NEUROFIBROMATOSIS IN SCHWANN CELLS

RELATED APPLICATION

This application claims priority from provisional application Ser. No. 60/946,782, which was filed on 28 Jun. 2007, and Ser. No. 60/955,141, which was filed on 10 Aug. 2007, both of which are incorporated herein by reference in their entirety.

STATEMENT OF GOVERNMENT RIGHTS

The work leading to this application was supported at least in part by a grant from the Department of Defense. Accordingly, the government may have certain rights in the invention, as specified by law.

FIELD OF THE INVENTION

This invention relates to the field of neurobiology and, more specifically, to therapeutic targets for treatment of neurofibromatosis type 2 (NF2).

BACKGROUND OF THE INVENTION

Neurofibromatosis is an autosomal dominant genetic disorder. It encompasses a set of distinct genetic disorders that cause tumors to grow along types of nerves and, in addition, can affect the development of non-nervous tissues such as bones and skin. The tumors can grow anywhere on or in the body. Apart from the common form, there are two rarer forms and several even rarer forms. Neurofibromatosis type I (was known as Von Recklinghausen disease after Friedrich Daniel von Recklinghausen) has an incidence of 1:3500. Neurofibromatosis type II (or "MISME Syndrome") has an incidence of 1:40,000.

Schwannomatosis is a rare form that is clinically and genetically distinct from types I and II. Multiple Schwannomas (rather than Neurofibromas) occur, and about one-third of patients have these tumors in only one part of the body. Incidence is 1:40,000. The vestibular nerve is spared. Pain is the primary symptom, although numbness, tingling and weakness can also occur. Schwannomas are always benign. Additionally, six other, extremely rare, forms are also recognized but won't be discussed here.

Symptoms of these Diseases

Neurofibromatosis type 1, is a mutation of neurofibromin chromosome 17q11.2. Symptoms include multiple neurofibromas on the skin and under the skin, the sub-cutaneous lumps are characteristic of the disease and increase in number with age; freckling of the groin and the arm pit; a predisposition to particular tumors (both benign and malignant); Café au lait spots (pigmented birthmarks). Six or more of these symptoms form one of the diagnostic criteria, but are not essential for diagnosis. Skeletal abnormalities such as scoliosis or bowing of the legs might occur. Also occurring are Lisch nodules (hamartomas of iris), tumor on the optic nerve and plexiform neurofibroma. Neurofibromatosis type 2, caused by mutation of merlin chromosome 22q12.

Other symptoms include bilateral tumors; acoustic neuromas on the vestibulocochlear nerve, as the hallmark of NF 2 is hearing loss due to acoustic neuromas around the age of twenty. The tumors may cause headache, balance problems, and Vertigo, facial weakness/paralysis. Patients with NF2 may also develop other brain tumors, as well as spinal tumors, deafness and tinnitus. Schwannomatosis, the gene involved has yet to be identified.

Multiple Schwannomas occur. The Schwannomas develop on cranial, spinal and peripheral nerves. Chronic pain is present, and sometimes numbness, tingling and weakness. About ⅓ of patients have segmental Schwannomatosis, which means that the Schwannomas are limited to a single part of the body, such as an arm, a leg or the spine. Unlike the other forums of NF, the Schwannomas do not develop on vestibular nerves, and as a result, no loss of hearing is associated with Schwannomatosis. Patients with Schwannomatosis do not have learning disabilities related to the disease.

Neurofibromatosis type 1 is due to mutation on chromosome 17q11.2, the gene product being Neurofibromin (a GTPase activating enzyme). Neurofibromatosis type 2 is due to mutation on chromosome 22q, the gene product is Merlin, a cytoskeletal protein. Both NF1 and NF2 are autosomal dominant disorders, meaning that only one copy of the mutated gene need be inherited to pass the disorder. A child of a parent with NF1 or NF2 and an unaffected parent will have a 50% chance of inheriting the disorder.

Complicating the question of heritability is the distinction between genotype and phenotype, that is, between the genetics and the actual manifestation of the disorder. In the case of NF1, no clear links between genotype and phenotype have been found, and the severity and specific nature of the symptoms may vary widely among family members with the disorder. In the case of NF2, however, manifestations are similar among family members; a strong genotype-phenotype correlation is believed to exist. Both NF1 and NF2 can also appear spontaneously through random mutation, with no family history. These spontaneous or sporadic cases account for about one half of neurofibromatosis cases.

SUMMARY OF THE INVENTION

With the foregoing in mind, the present invention advantageously provides a method for inducing neurofibromatosis type 2 (NF2) in Schwann cells. Accordingly, one utility of the invention is in providing a model of neurofibromatosis type 2 which, as known by the skilled, would allow for testing of new treatment drugs.

The method comprises contacting the cells with laminin-1 so as to bind α6β1 integrin sufficiently to activate endogenous kinase Cdc42-Pak; and, in response, phosphorylating Schwannomin-S518 in the cells by the activated kinase, effectively inactivating Schwannomin's tumor suppressor activity and allowing proliferation of subconfluent Schwann cells, thereby modeling NF2.

In another embodiment, the method of inducing neurofibromatosis type 2 (NF2), the method comprises contacting Schwann cells with NRG-1 so as to bind ErbB2 and/or ErbB3 receptors sufficiently to activate protein kinase A (PKA) and phosphorylating Schwannomin-S815 in the cells by the activated PKA effectively inactivating Schwannomin's tumor suppressor activity and allowing proliferation of subconfluent Schwann cells, thereby modeling NF2.

The invention further provides a method of preventing inactivation of Schwannomin's tumor suppressor activity in Schwann cells. This method comprises contacting the Schwann cells with an effective amount of a blocking agent that inhibits normal function of a receptor selected from ErB2, ErB3, β1 integrins and combinations thereof, thereby preventing phosphorylation of Schwannomin-S815 by one or more endogenous kinases. In this method the blocking agent preferably comprises a tyrphostin and, particularly, tyrphostin AG825.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which the following figure descriptions apply.

DETAILED DESCRIPTION OF THE PREFERRED EMBODIMENT

Figure 1:
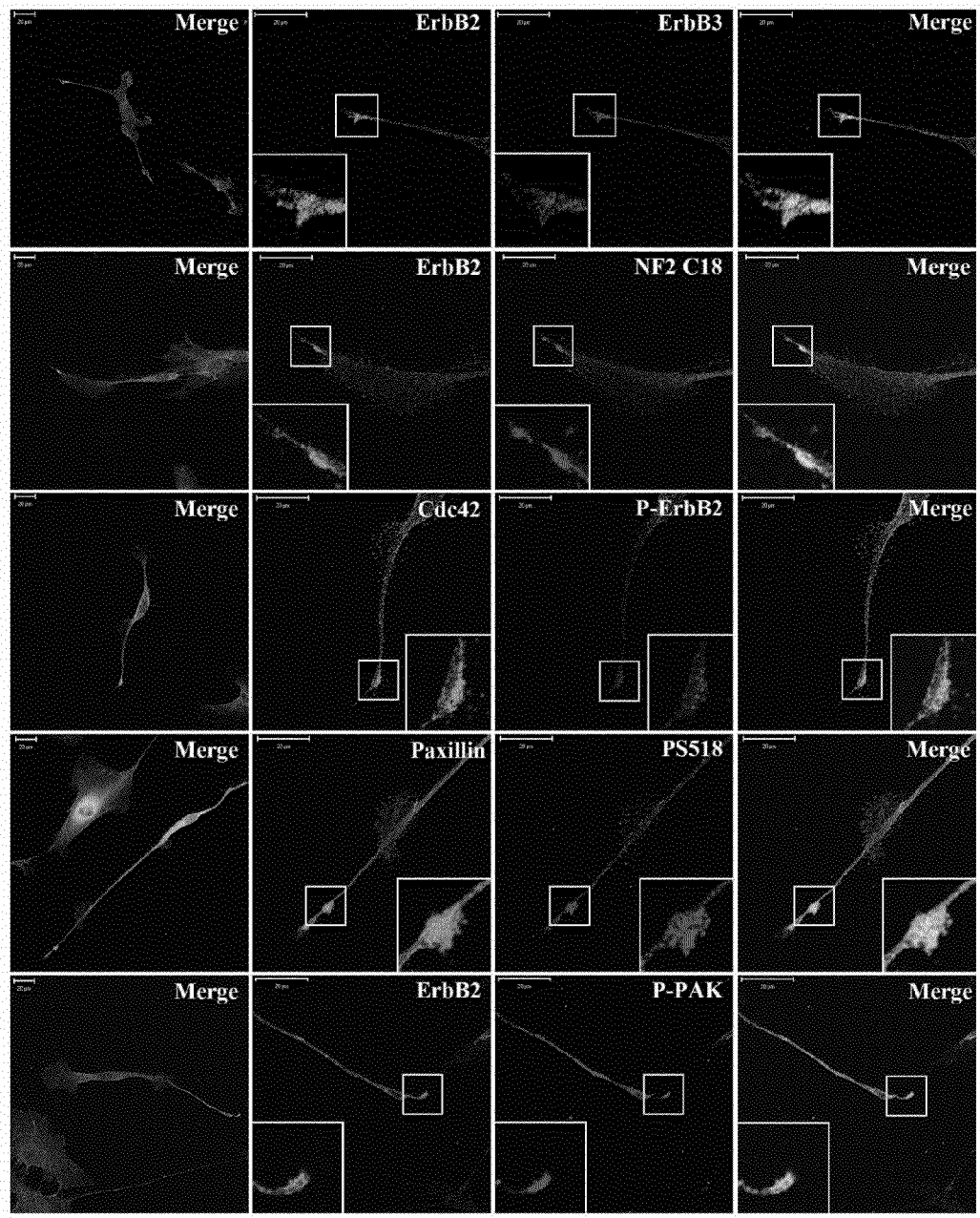
FIG. 1 shows phosphorylated forms of ErbB2, Sch, and Pak co-localize with paxillin and Cdc42 in processes, their distal tips and radial protrusions following acute stimulation with NRG. Subconfluent SCs plated on PLL/laminin-1 coated coverslips were serum-starved overnight and were then stimulated with NRG1 for 30 minutes. Immunostaining was conducted for the indicated proteins to assess phosphorylation status and localization. All proteins were found in SC processes and were focally enriched at radial membrane protrusions and distal tips.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Abbreviations used herein are as follows: cyclic-AMP response element binding protein (P-CREB); Neurofibromatosis type 2 (NF2); p21-activated kinase (Pak); neuregulin-1 (NRG1); protein kinase A (PKA); Schwann cells (SCs); and Schwannomin (Sch).

The Neurofibromatosis type 2 (NF2) tumor suppressor Schwannomin (Sch), also known as merlin, is a membrane-cytoskeleton linking protein (Rouleau et al., 1993; Trofatter et al., 1993). Mutations in the NF2 gene predispose individuals to benign, slow-growing schwannomas. Sch's conformation, localization, and phosphorylation are important determinants of its ability to regulate proliferation and actin organization (reviewed in McClatchey and Giovannini, 2005). The tumor suppressor function of Sch is associated with its closed, intracellular form lacking phosphorylation on serine 518 (S518; Rong et al., 2004; Shaw et al., 2001). In this conformation, Sch inhibits Rac-mediated signaling cascades and progression through the G1 phase of the cell cycle (reviewed in Okada et al., 2007). Phosphorylation of Sch-S518 is believed to stabilize Sch in the open conformation, inhibiting its tumor suppressor function while unmasking binding sites for transmembrane receptors and actin-associated proteins (James et al., 2001; Rong et al., 2004). P21-activated kinase (Pak) and protein kinase A (PKA) phosphorylate Sch on S518, but the receptor mechanisms leading to Sch phosphorylation are unknown (Kissil et al., 2002; Xiao et al., 2002; Alfthan et al., 2004).

Previously, we demonstrated that Sch localization to the plasma membrane, and its phosphorylation on S518 requires direct binding of residues 50-70 within Sch's N-terminus to the scaffold protein, paxillin (Fernandez-Valle et al., 2002, Thaxton et al., 2007). We also demonstrated that Sch is present at the plasma membrane of subconfluent Schwann cells (SCs), where Sch and paxillin interact with β1 integrin and ErbB2; receptors critical for SC adhesion, motility, proliferation and myelination (Fernandez-Valle et al., 2002; reviewed in Garratt et al., 2000; reviewed in Chernousov and Carey, 2000). Paxillin also recruits Pak to the plasma membrane, and serves as a scaffold for Sch-Pak interactions by binding multiple regulators of Rac and Cdc42, members of the Rho family of GTPases, as well as actin binding proteins and components of focal complexes and adhesions (reviewed in Turner, 2000).

Here, we demonstrate that NRG1 and laminin-1, ligands for ErbB and β1 integrin receptors, respectively, induce Sch phosphorylation in SCs through two independent pathways, NRG1 by PKA, and laminin by Pak. NRG1 and laminin-1 do not synergize to increase Sch phosphorylation, but rather NRG1 through PKA partially antagonizes laminin-induced, and Pak-mediated Sch phosphorylation. These findings show that Sch is a convergence point for transduction of signals from ErbB and β1 integrin receptors that regulate proliferation, differentiation and cytoskeletal dynamics in SCs during peripheral nerve development.

Material and Methods

Materials

The following materials were used: Natural mouse laminin-1 and Lipofectamine 2000 (Invitrogen; Carlsbad, Calif., USA), AG825 and PKI 14-22 amide (EMD Biosciences; San Diego, Calif., USA). Sch-GFP constructs were described previously (Thaxton et al., 2007). Recombinant human NRG-1 beta/type II was a generous gift from Mark Marchionni. Myc-Pak K299A and Myc-Pak L107F. T423E (Myc-Pak T423E) constructs were generous gifts from Gary Bokoch (The Scripps Research Inst., La Jolla, Calif., USA). Antibodies were purchased from the following sources: ErbB2 and Sch (C18) from Santa Cruz Biotechnology (Santa Cruz, Calif., USA); β1 integrin from BD Transduction Labs (San Jose, Calif., USA); Pak, Myc, and P-CREB from Cell Signaling (Boston, Mass., USA); PS518-Sch and P-ErbB2 (Y1248) from Abcam (Cambridge. Mass., USA); P-Pak (T423) from Rockland Immunologicals, Inc. (Gilbertsville, Pa., USA); Xpress from Invitrogen; ErbB2 from EMD Biosciences; and Alexa Fluor conjugated secondary antibodies from Invitrogen.

Cell Culture

Primary rat SC cultures were prepared from neo-natal day 1 rat pups as described previously (Chen et al., 2000). Subconfluent SC cultures were grown on glass coverslips coated with poly-L-lysine (PLL; 200 mg/ml) alone or sequentially with laminin-1 (25 mg/ml). Cultures were starved overnight in Dulbecco's Modified Eagle Medium (DME) with 0.5% fetal bovine serum (D0.5) before use. The SCs were either left unstimulated, or were stimulated with NRG (10 ng/ml) for 30 minutes. For laminin-1 stimulation, primary rat SCs were grown on PLL coated glass coverslips and were starved overnight in D0.5. The SCs were then stimulated with soluble laminin-1 (10 mg/ml) or were left unstimulated.

Immunostaining

The SCs were immunostained as described previously (Fernandez-Valle, 2002). Cells were analyzed with a Zeiss laser scanning microscope and LSM 510 software. Images shown in each figure are single planes, and were collected with identical settings, and were processed identically.

Western Blotting

Primary rat SCs were grown to approximately 60% confluency on PLL coated dishes. The cultures were serum starved overnight in D0.5 and were either left in D0.5 or were pre-incubated with AG825 (1 mM) or PKI 14-22 (50 nM) for 1 hour. Next, the SCs were either left unstimulated or were stimulated with NRG1 (10 ng/ml) and/or laminin-1 (10 mg/ml) in the presence and absence of AG825 (1 mM) or PKI 14-22 (50 nM) for 30 minutes. The SCs were extracted as described previously (Fernandez-Valle et al., 2002) in either TAN buffer (10 mM Tris-acetate pH8.0, 100 mM NaCl, and 1% IGEPAL) or HEPES buffer (50 mM HEPES, 1 mM DTT, 150 mM NaCl, 1% IGEPAL) containing protease inhibitors. Following extraction, the SC lysate was measured for protein concentration, and 10 mg of total SC lysate was separated by SDS-PAGE and was transferred to PVDF membranes. The indicated primary antibodies were used, followed by corresponding HRP-conjugated secondary antibody and chemiluminescence detection. Densitometric analysis was conducted on all Western blots. Bands intensities were quantified and normalized to GAPDH, and to their respective total proteins for phosphorylated forms. Statistical analysis was acquired using the Student t-test by paired analysis.

Immunoprecipitation

Subconfluent SC cultures grown in medium containing 10% FBS, forskolin (2 mM) and pituitary extract (20 mg/ml) were extracted in TAN buffer and 500 mg of lysate were immunoprecipitated with β1 integrin antibody, as described previously (Chen et al., 2000). Immunoprecipitation with 31 integrin antibody covalently linked to magnetic beads was performed as described previously (Taylor et al., 2003).

Transfections

Primary rat SC cultures were transfected using Lipofectamine 2000 as described previously (Thaxton et al., 2007). Thirty-six hours after transfection, the SCs were immunostained.

Results

NRG and Laminin Induce Phosphorylation of Sch at SC Distal Tips and Radial Membrane Protrusions NRG and laminin activate Cdc42/Rac GTPases and Pak in other cell types (Adam et al., 1998; Del Pozo et al., 2000). Work from this laboratory has demonstrated that Sch can interact with both ErbB2 and β1 integrin, and that paxillin-dependent localization to the plasma membrane is required for phosphorylation of Sch by Cdc42-Pak (Fernandez-Valle et al., 2002; Thaxton et al. 2007). Here, we sought to identify receptor(s) that trigger Pak activity and Sch phosphorylation. We stimulated subconfluent and serum-starved primary rat SCs grown on laminin-1 with NRG1 for 30 minutes, and assessed the phosphorylation states and localization of ErbB2, Sch and Pak. ErbB2, ErbB3, and Sch were found along SC processes, and were concentrated at the distal tips. NRG1 stimulation induced a focal enrichment of P-ErbB2 and PS518-Sch at the distal tips of SC processes and within membrane protrusions (FIG. 1). These molecules co-localized with Cdc42 and paxillin. Phosphorylated Pak was also enriched in membrane protrusions and at the distal tips where it co-localized with ErbB2.

Figure 2:
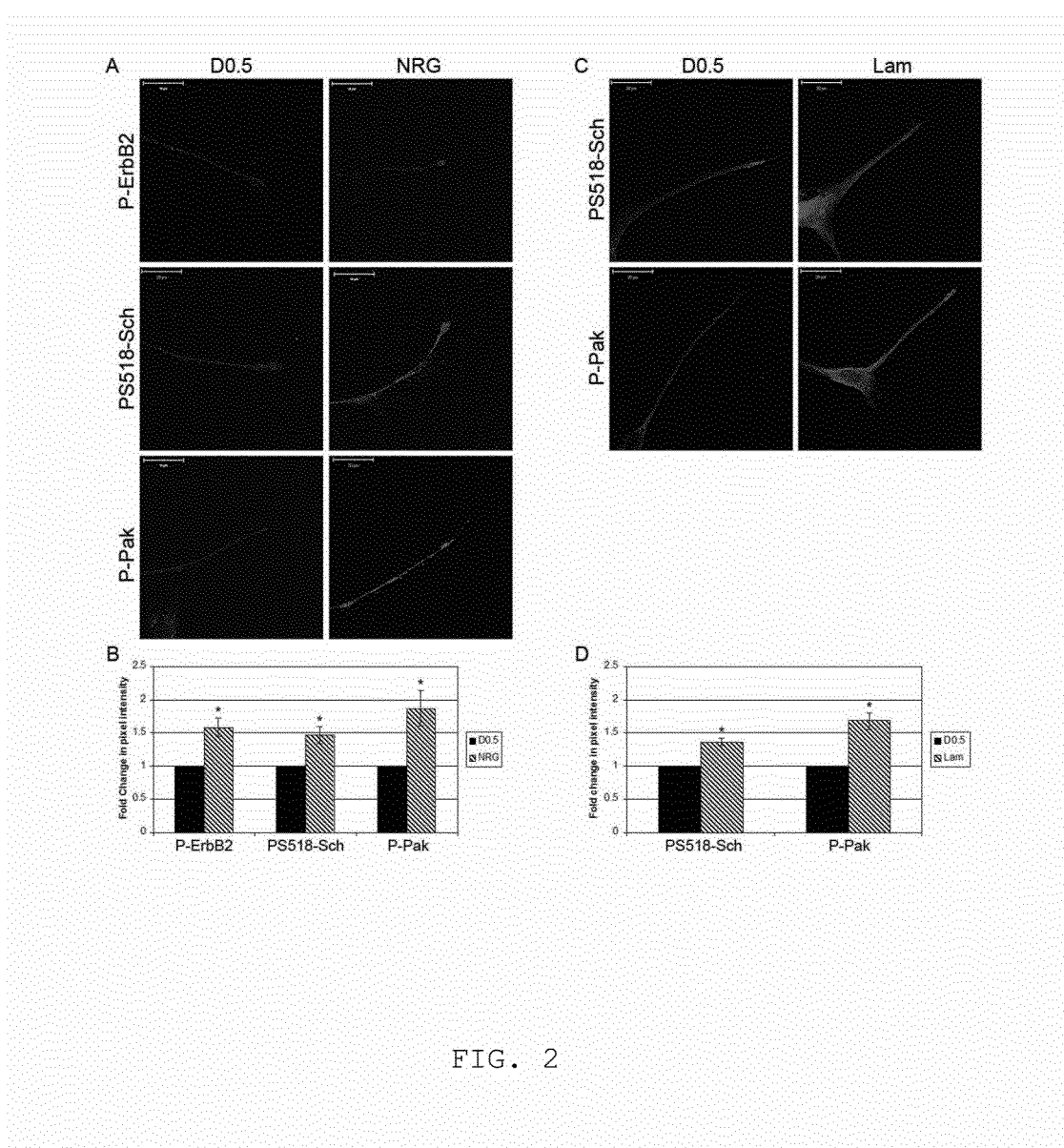
FIG. 2: NRG1 and Laminin-1 Induce Sch Phosphorylation in SC Processes. A) Subconfluent SCs grown on PLL/laminin-1 were starved overnight (D0.5) and were left untreated, or were stimulated for 30 minutes with NRG1 (10 ng/ml). Phosphorylation of ErbB2 (P-ErbB2), Sch (PS518-Sch), and Pak (P-Pak) was assessed by immunostaining with phosphospecific antibodies. B) Quantification of mean fluorescence intensity in 15-20 isolated SC processes per condition is shown. C) Subconfluent SCs grown on PLL were starved overnight and were left untreated (D0.5), or were stimulated with soluble laminin-1 (Lam; 10 mg/ml) for 30 minutes. SCs were immunostained with the indicated antibodies. D) Quantification of the change in mean fluorescence intensity in 15-20 isolated SC processes per condition is shown. The graphs represent the average fold increase in each condition in three or more experiments. Error bars represent the SEM for each condition. P values are <0.05(*).

We quantified the changes in phosphorylation of ErbB2, Sch, and Pak in serum starved and NRG1 stimulated SC processes (FIG. 2 A, B). We found marked increases in fluorescence intensity along SC processes for P-ErbB2, PS518-Sch, and P-Pak, particularly at process tips of stimulated versus starved SCs (FIG. 2A). P-ErbB2 levels increased by 1.6-fold, PS518-Sch by 1.5-fold, and P-Pak by 1.9-fold in NRG1 stimulated versus starved SCs (FIG. 2 B). These results demonstrate that acute stimulation of SCs with NRG1 induces phosphorylation of Sch downstream of ErbB2/ErbB3, possibly by Pak.

As the SCs were grown on laminin-1, a ligand for β1 integrin that mediates SC adhesion (Fernandez-Valle et al., 1994), we tested whether a 30-minute exposure to soluble laminin-1 stimulated Sch phosphorylation in subconfluent and serum-starved SCs grown on PLL. Laminin-1 promoted a strong increase in Sch and Pak phosphorylation compared to starved SCs (FIG. 2 C). Quantification of fluorescence intensity along the processes revealed a 1.4-fold increase in PS518-Sch and a 1.7-fold increase in P-Pak compared to untreated SCs (FIG. 2 D). These results demonstrate that adhesion to laminin-1 induces Sch phosphorylation at the plasma membrane, possibly by Pak.

NRG Promotes Sch Phosphorylation Through PKA

Figure 3:
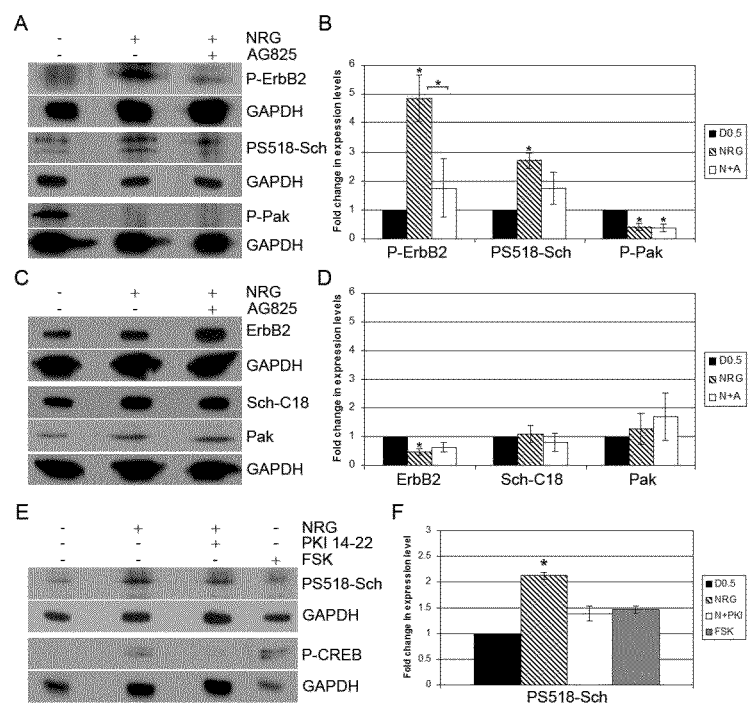
FIG. 3: NRG1 stimulates phosphorylation of Sch by PKA. A, C) Subconfluent SC cultures grown on PLL were serum-starved overnight and were stimulated for 30 minutes with NRG1 (10 ng/ml) in the absence and presence of AG825 (1 µM). Western blot analysis was used to determine the levels of phosphorylated and total ErbB2, Sch, and Pak. B, D) Quantification of the western blots of starved (D0.5), NRG1 stimulated (NRG) and NRG1 plus AG825 (N+A) stimulated cultures is shown. E) Subconfluent SCs grown as above were stimulated for 30 minutes with NRG in the presence and absence of PKI 14-22 (50 nM), and with forskolin (FSK; 2 µM) alone. F) Quantification of the Western blots for ErbB2, Sch, and Pak in starved (D0.5) cultures, and in those stimulated with NRG1 (NRG), NRG1 with PKI 14-22 (N+P), and forskolin (FSK) is shown. GAPDH was used as a loading control for all blots. The graphs represent the average fold increase in each condition in three or more experiments. Error bars represent the SEM for each condition. P values are <0.05 (*) with respect to starved SCs or as indicated.

To determine the relative contributions of ErbB2/ErbB3 and β1 integrin activation on Sch phosphorylation, we repeated the experiments using SCs plated on PLL rather than laminin-1, and employed the use of AG825 to specifically inhibit ErbB2 kinase activity (Osherov et al., 1993). Subconfluent SCs were starved and then were stimulated with NRG1 in the presence and absence of AG825 (FIG. 3). NRG1 promoted a 4.8-fold increase in P-ErbB2 and a 2.7-fold increase in PS518-Sch compared to starved SCs. AG825 reduced NRG1 stimulated phosphorylation of ErbB2 significantly, as well as Sch-S518 phosphorylation (FIG. 3A, B). Surprisingly, no Pak phosphorylation was observed in NRG1 stimulated SCs. When total protein levels were assessed, we found that stimulation with NRG1 reduced the amount of ErbB2 by 50% (FIG. 3C, D). This is consistent with rapid, ligand-induced degradation of ErbB2 receptors (Lotti et al., 1992). AG825 attenuated the reduction in ErbB2 levels. These results suggest that NRG1 triggers Sch phosphorylation independently of Pak in SCs.

PKA has been reported to phosphorylate Sch at S518 in vitro (Alfthan et al., 2004). Additionally, NRG1 stimulation has been suggested to induce PKA activity in SCs (Kim et al., 1997). Therefore, we tested whether PKA phosphorylated Sch in response to NRG1 activation of ErbB2/ErbB3 receptors on SCs. Subconfluent SCs were serum starved and were stimulated with NRG1 in the presence and absence of PKI 14-22 amide, a specific inhibitor of PKA activity (FIG. 3 E, F). NRG1 alone stimulated a 2.1-fold increase in phosphorylated Sch compared to starved SCs, and induced phosphorylation of the cyclic-AMP response element binding protein (P-CREB), a known substrate for PKA. PKI 14-22 reduced the levels of Sch and CREB phosphorylation to near basal levels observed in starved controls. Additionally, stimulation of starved SCs for 30 minutes with forskolin, an activator of adenylyl cyclase that increases intracellular cyclic-AMP and activates PKA, also induced phosphorylation of Sch and CREB. These results provide evidence for PKA-dependent phosphorylation of Sch following NRG1 binding to ErbB2/ErbB3 in SCs.

Laminin Promotes Phosphorylation of Sch-S518 by Pak

Figure 4:
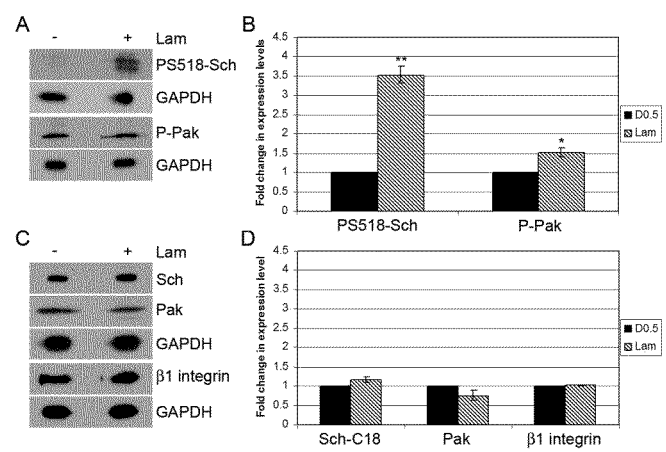
FIG. 4: Soluble Laminin-1 Stimulates Phosphorylation of Sch. A, C) Subconfluent SC cultures grown on PLL were stimulated with laminin-1 (10 µg/ml) for 30 minutes after overnight serum starvation. Western blot analysis using antibodies specific for the phosphorylated forms of Sch (PS518-Sch) and Pak (P-Pak) and antibodies against total Sch (Sch-C18), Pak, and β1 integrin are shown. B, D). Quantification of Western blots for starved (D0.5) and laminin-1 stimulated (Lam) cultures is shown. The graphs represent the average fold increase in each condition observed in three or more experiments. GAPDH was used as a loading control for all blots. Error bars represent the SEM for each condition. P values are <0.05(*) and <0.01(**).

To determine if laminin-1 induced phosphorylation of Sch by Pak, we stimulated SCs grown on PLL with soluble laminin-1 for 30 minutes and conducted western blot analyses (FIG. 4). Laminin-1 promoted a substantial 3.5-fold increase in Sch-S518 phosphorylation and a 1.5-fold increase in Pak phoshorylation compared to starved SCs (FIG. 4 A, B). The levels of total Sch and β1 integrin did not significantly change in response to laminin-1, while the levels of total Pak fell by 25% (FIG. 4 C, D). We additionally tested whether laminin-1 activated ErbB2 and PKA. Laminin-1 stimulated SCs had no change in the basal level of P-ErbB2 and did not contain P-CREB (data not shown). These findings are consistent with Pak mediated phosphorylation of Sch-S518 following laminin binding to β1 integrins expressed on the surface of subconfluent SCs.

Figure 5:
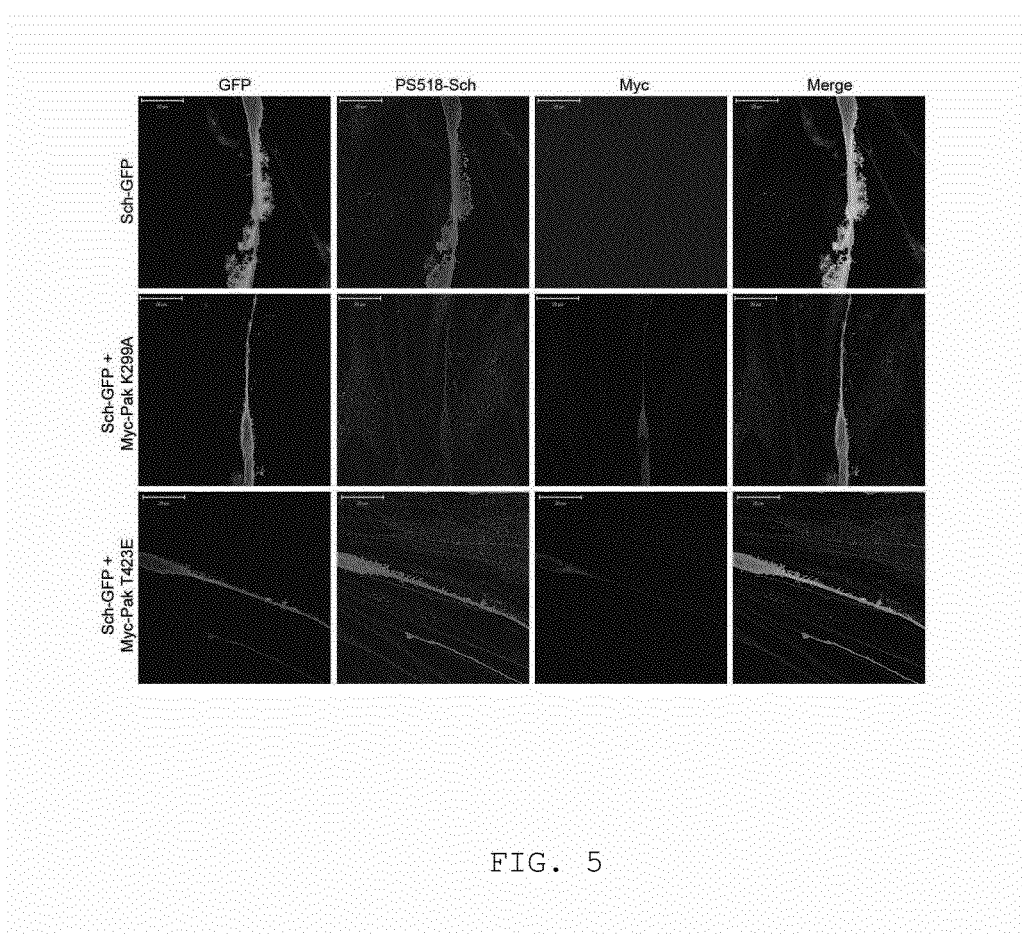
FIG. 5: Catalytically Inactive Pak Inhibits Sch Phosphorylation in SCs Adhering to Laminin-1. SCs plated on PLL and laminin-1 were transiently transfected with GFP-tagged full length Sch (Sch-GFP) alone or with Myc-tagged catalytically inactive Pak (Myc-PakK299A) or Myc-tagged constitutively active Pak (Myc-PakT423E), and were immunostained to assess Sch-S518 phosphorylation (PS518-Sch) and Myc-Pak expression (Myc).
Figure 6:
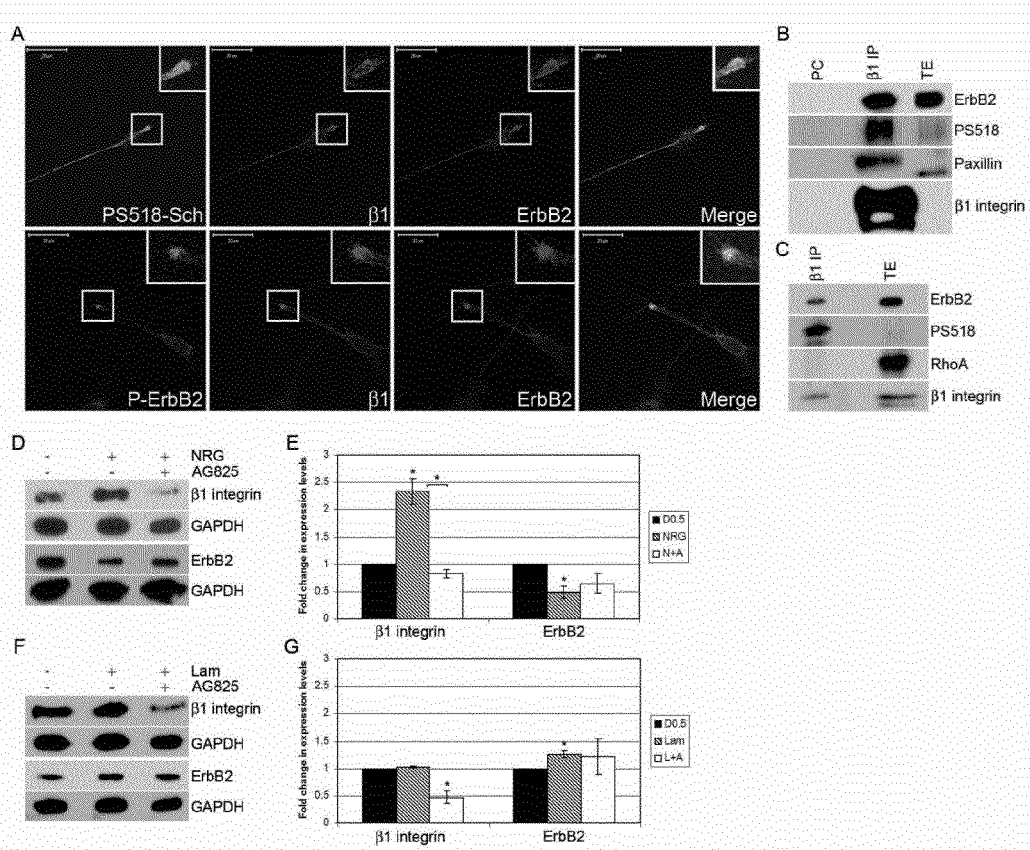
FIG. 6: β1 integrin and ErbB2 Exist as a Complex on the Plasma Membrane. A) Subconfluent SC cultures grown on PLL and laminin-1 were starved overnight and were stimulated with NRG1 for 30 minutes. SCs were triple-labeled with the indicated antibodies to assess protein co-localization. B) Subconfluent SC cultures were extracted and lysates (TE) were pre-cleared (PC) with normal IgG and were immunoprecipitated with β1 integrin antibody (β1 IP). Western blots analysis was conducted with the indicated antibodies. C) Intact SCs in suspension were incubated with β1 integrin antibody immobilized on magnetic beads to induce clustering. SCs were lysed, and the immunoprecipitate (β1IP) and total protein lysate (TE) were immunoblotted with the indicated antibodies. D) Subconfluent and serum-starved SCs grown on PLL were stimulated for 30 minutes with NRG1 (10 ng/ml) in the presence and absence of AG825 (1 µM). Western blot analysis was conducted with the indicated antibodies. E) Quantification of total β1 integrin and ErbB2 expression was assessed by densitometry in starved (D0.5), NRG1 stimulated (NRG) and NRG with AG825 (N+A) stimulated cultures. F) Subconfluent SCs were starved overnight in D0.5 and then were stimulated for 30 minutes with laminin-1 (10 mg/ml) in the presence and absence of AG825 (1 µM). Western blot analyses were conducted to examine changes in receptor expression levels. G) Quantification of total β1 integrin and ErbB2 expression in starved (D0.5), laminin-stimulated (Lam) and laminin+AG825 (L+A) stimulated cultures is shown. GAPDH was used as a loading control for all blots. The graphs represent the average fold increase in each condition in three or more experiments. Error bars represent the SEM for each condition. P values are <0.05(*) with respect to starved SCs or as indicated.

To obtain additional evidence that Pak phosphorylates Sch in response to stimulation with laminin-1, we transiently transfected SCs plated on PLL and laminin-1 with GFP-tagged Sch and Myc-tagged Pak kinase mutant constructs (FIG. 5). As shown previously, expression of wild-type Sch (Sch-GFP) resulted in Sch phosphorylation at the plasma membrane within discrete membrane protrusions that contain P-Pak (Thaxton et al., 2007). Co-expression of Sch-GFP with catalytically inactive Pak (Myc-Pak K299A) resulted in a loss of PS518-Sch fluorescence in these domains and throughout the SC, whereas co-expression with constitutively active Pak (Myc Pak T423E) resulted in unrestricted Sch phosphorylation. These results support Pak-mediated phosphorylation of Sch induced by β1 integrin adhesion to laminin-1.

β1 integrin and ErbB2 Exist as a Functional Co-Receptor Complex on the SC Surface To investigate the possibility that ErbB2 and β1 integrin act as co-receptors to regulate Sch phosphorylation, we tested their ability to co-localize and co-immunoprecipitate. We found that β1 integrin and ErbB2 co-localized with PS518-Sch and P-ErbB2 at the distal tips of SC processes acutely stimulated with NRG1 (FIG. 6 A). β1 integrin immunoprecipitations prepared from lysates of subconfluent SC cultures contained β1 integrin and ErbB2, as well as, PS518-Sch and paxillin (FIG. 6 B). To ascertain whether the receptors associated on the cell surface, (31 integrins were clustered on suspended intact SCs using a β1 integrin antibody immobilized on magnetic beads and were subsequently lysed and the clustered receptor complexes were isolated (FIG. 6 C). A subset of ErbB2 receptors and PS518-Sch were present in the β1 integrin immunoprecipitate. RhoA, used as a control, was not present in the immunoprecipitate.

Trans-activation of integrins and receptor tyrosine kinases occurs, and can produce changes in receptor protein expression (reviewed in Lee and Juliano, 2004). To determine if this occurs in SCs, β1 integrin and ErbB2 protein levels were measured following stimulation with NRG1 or laminin-1 for 30 minutes. Stimulation with NRG1 significantly increased β1 integrin levels 2.3-fold, but decreased ErbB2 levels by half as compared to starved SCs (FIG. 6 D, E). Stimulation of SCs with NRG1 and AG825 suppressed NRG1's effect on both β1 integrin and ErbB2 protein levels. Stimulation of SCs with laminin-1 did not alter β1 integrin protein levels, but did increase ErbB2 protein levels by a statistically significant 1.3-fold compared to untreated SCs (FIG. 6 F, G). Surprisingly, stimulation with laminin-1 and AG825 decreased β1 integrin levels by 50%, but did not alter ErbB2 levels with respect to laminin-stimulated SCs. This is consistent with a basal level of autocrine activation of ErbB2/ErbB3 in SCs. SCs have been shown to synthesize and secrete NRGs in response to serum deprivation, thereby transducing survival signals (Rosenbaum et al., 1997).

Figure 7:
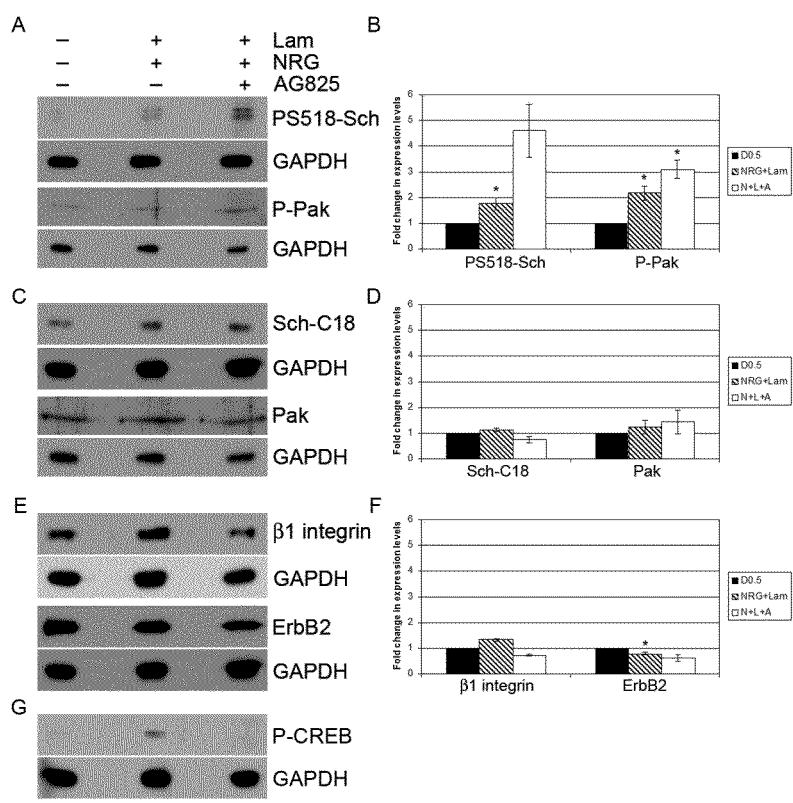
FIG. 7: AG825 Increases Sch Phosphorylation in Response to Laminin-1 and NRG1. Subconfluent SC cultures grown on PLL were serum-starved overnight and were stimulated for 30 minutes with NRG1 (10 ng/ml) and laminin-1 (10 mg/ml) together, in the absence and presence of AG825 (1 µM). A, C, E, G) Western blot analyses were conducted using phosphospecific antibodies for Sch (PS518-Sch), Pak (P-Pak), and CREB (P-CREB). Total protein expression was analyzed using antibodies against Sch (Sch-C18), Pak, β1 integrin, and ErbB2. B, D, F) Quantification of the expression levels of phosphorylated forms of Sch (PS518-Sch) and Pak (P-Pak) were assessed in starved (D0.5), NRG1 and laminin-1 stimulated (NRG+Lam), and NRG1 plus laminin-1 and AG825 (N+L+A) stimulated cultures. The amount of total Sch (Sch-C18), Pak, β1 integrin, and ErbB2 proteins were measured by densitometry. GAPDH was used as a loading control. The graphs represent the average fold increase in each condition in three or more experiments. Error bars represent the SEM for each condition. P values are <0.05(*) with respect to starved SCs, or as indicated.
Figure 8:
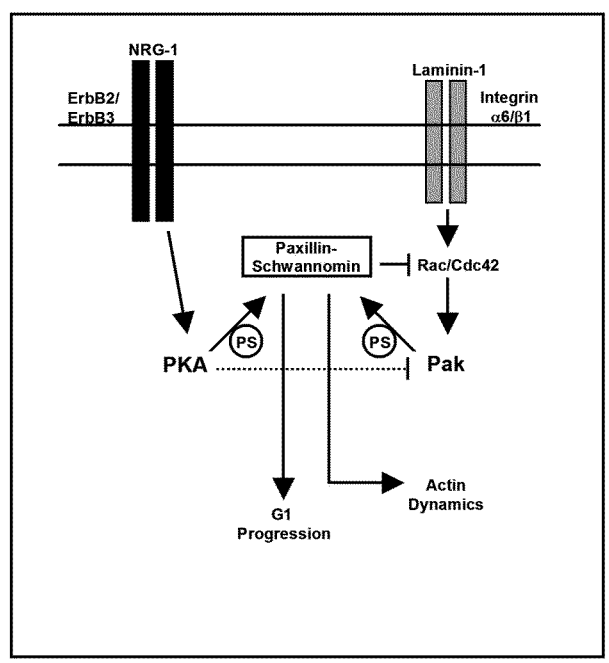
FIG. 8: Model of ErbB and β1 Integrin Induced Phosphorylation of Sch and Inactivation of its Tumor Suppressor Function in Subconfluent SCs. Unphosphorylated Sch restricts proliferation by inhibiting activation of the Rac-Pak pathway in confluent cells. In a regulatory loop, Pak phosphorylates Sch, inactivating its tumor suppressor ability. In subconfluent SCs. Sch is phosphorylated in response to activation of ErbB2/ErbB3 and α6β1 integrin receptors by NRG1 and laminin-1, respectively. through two distinct pathways involving PKA and Pak. Simultaneous co-activation of both receptors does not synergistically increase Sch phosphorylation but rather ErbB2, through PKA, inhibits Pak phosphorylation of Sch (dashed line). Phosphorylated Sch is unable to inhibit Rac-Pak and allows transduction of ErbB and α6β1 integrin signals that promote G1 progression. Additionally, the presence of this complex at the motile distal tip of SC processes coordinates motility along axons and other cytoskeletal changes in response NRG and basal lamina necessary for myelination of peripheral nerves during development.

Dual Stimulation with NRG and Laminin does not Synergistically Increase Sch Phosphorylation To determine if simultaneous activation of ErbB2/ErbB3 and β1 integrin in SCs synergize to increase phosphorylation of Sch, we stimulated serum-starved SCs grown on PLL for 30 minutes with NRG1 and soluble laminin-1, in the presence and absence of AG825 (FIG. 7). Dual stimulation resulted in a significant 1.8-fold increase in PS518-Sch and a 2.1-fold increase in P-Pak compared to unstimulated SCs. This level of Sch phosphorylation was not higher than levels observed in SCs stimulated with either NRG1 or laminin-1 alone, which were 2.7-fold and 3.5-fold higher than starved SCs, respectively (FIG. 7 A, B). Surprisingly, stimulation with NRG1 and laminin-1 in the presence of AG825 promoted greater phosphorylation of Sch-S518 (a 4.6-fold increase) and Pak (a 3.1-fold increase) compared to starved SCs, suggesting that ErbB2 kinase activity partially inhibits Pak and its phosphorylation of Sch. PKA has been shown to directly phosphorylate and inhibit Pak (Howe and Juliano, 2000). We found that AG825 inhibited phosphorylation of CREB in response to NRG1 in dually stimulated SCs, consistent with PKA inhibition of Pak (FIG. 7 G). Sch, Pak and β1 integrin protein levels were not significantly changed in SCs stimulated with NRG1 and laminin-1 in the presence and absence of AG825 (FIG. 7 C, D). Stimulation with NRG1 and laminin-1 resulted in a 30% decrease in ErbB2 compared to starved SCs. This result indicates that PKA activated downstream of ErbB2 kinase activity partially inhibits Pak-dependent phosphorylation of Sch in response to laminin-1. A model consistent with our results is shown (FIG. 8).

Discussion

Phosphorylation of S518 is a critical switch that controls Sch's tumor suppressor activity. Pak and PKA have been shown to phosphorylate Sch on S518 when overexpressed with Sch in cell lines and in in vitro kinase assays, but neither kinase has been linked to receptor activation and phosphorylation of endogenously expressed Sch in any cell type (Kissil et al., 2002; Xiao et al., 2002; Alfthan et al., 2004). Here, we identify two receptors that lead to rapid phosphorylation of Sch-S518 in SCs. Laminin-1 binding to β1 integrin activates Pak, whereas NRG1 binding to ErbB receptors activates PKA. Each kinase phosphorylates Sch-S518 within 30 minutes of stimulation. Both receptors regulate all stages of Schwann cell development including proliferation, and both play central roles in the tumorigenic and metastatic capacities of many additional cell types.

Two Distinct Receptor Mediated Pathways Promote Sch Phosphorylation

Our data provide strong evidence that NRG1 binding to ErbB2/ErbB3 induces PKA-dependent phosphorylation of endogenous Sch. This conclusion is supported by the following results. First, serum-starved SCs have basal levels of phosphorylated Pak and Sch. NRG1 inhibits basal Pak activity while increasing the amount of phosphorylated Sch, 2.7-fold. Second, inhibition of ErbB2 kinase activity by AG825 reduces Sch-S518 phosphorylation in response to NRG1 by 50%. Third, the PKA inhibitor, PKI 14-22 similarly reduces Sch-S518 phosphorylation in response to NRG1 by 70%. Lastly, although not as effective as NRG1, forskolin increases Sch phosphorylation. We also show that NRG1 promotes phosphorylation of CREB and that both AG825 and PKI 14-22 inhibit this phosphorylation, consistent with NRG stimulation of PKA activity. In support, others have also found evidence of PKA activation by NRG in SCs (Kim et al., 1997). Overall, our results indicate that NRG binds to ErbB2/ErbB3 receptors and stimulates rapid phosphorylation of Sch on S518 by PKA.

Cell adhesion to extracellular matrix through integrins activates Pak (Del Pozo et al., 2000). Laminin-1 is present in the endoneurium of nerves in perinatal mice, and promotes strong in vitro adhesion, migration and proliferation of SCs (Milner et al., 1997; Dubovy et al., 2000). Previously we demonstrated that α6β1 integrin is the predominant laminin-1 binding integrin present in SCs at this stage of development (Fernandez-Valle et al., 1994). Our new findings indicate that laminin-1 binding to α6β1 integrin promotes Sch-S518 phosphorylation by Pak. Our evidence is as follows: First, stimulation of SCs with soluble laminin-1 increases both P-Pak (1.5-fold) and PS518-Sch (3.5-fold) over basal levels. Similarly, P-Pak and PS518-Sch are increased within SC processes as assessed by quantification of immunofluorescence. Second, Sch-GFP expressed in SCs adhering to laminin-1 is phosphorylated by an endogenous kinase, predominantly when localized at the plasma membrane of cellular processes and particularly in radial membrane protrusions. Previously, we reported that Cdc42-Pak rather than Rac-Pak was associated with phosphorylation of Sch in these domains (Thaxton et al., 2007). Consistently, we find that expression of catalytically inactive Pak inhibits phosphorylation of Sch-GFP in SCs adhering to laminin-1. Lastly, laminin-1 does not activate PKA or trans-activate ErbB2, as P-ErbB2 and P-CREB were not found, ruling out PKA dependent phosphorylation of Sch in response to laminin-1. It has been established that Pak is recruited to focal complexes through an indirect interaction with paxillin, stimulated by Cdc42 and Rac activity (Brown et al., 2002). Together, our results indicate that aggregation of α6β1 integrins by laminin-1 triggers translocation of a Pak-paxillin-Sch complex to nascent focal complexes where Sch-S518 is phosphorylated by Cdc42-Pak.

ErbB2 Modulates β1 Integrin Signaling

Our data demonstrate that ErbB2/ErbB3 and β1 integrin physically interact and function as co-receptors that regulate both the turnover rate of each receptor and their downstream signals. ErbB2/ErbB3 and β1 integrin co-immunoprecipitate and co-localize on the SC surface and are enriched at the distal tips of SC processes stimulated with NRG1. Simultaneous activation of ErbB2/ErbB3 and β1 integrin receptors does not synergistically increase Sch phosphorylation, but rather ErbB2 activity appears to antagonize Pak-dependent phosphorylation of Sch. In SCs stimulated with NRG1, laminin-1 and AG825, PS518-Sch and P-Pak levels increase over dually stimulated SCs while P-CREB is eliminated. AG825, in the absence of NRG1 also increases basal levels of phosphorylated Pak and Sch (data not shown), consistent with autocrine stimulation of ErbB2 and PKA activity (Rosenbaum et al., 1997). PKA has been shown to directly phosphorylate and inhibit Pak in NIH3T3 cells (Howe and Juliano, 2000). Together, these findings indicate that ErbB2, through PKA, antagonizes Pak dependent phosphorylation of Sch downstream of β1 integrin.

Implications for Schwannoma Development

β1 integrin and ErbB receptors regulate SC proliferation during development. Conditional inactivation of genes encoding their respective ligands, the laminin g1 gene and the neuregulin gene, in mice are associated with low proliferative capacity of SCs during development, demonstrating that both receptors are essential for SC proliferation (reviewed in Garratt et al., 2000; Chen and Strickland, 2003; Yang et al., 2005). Cooperation between receptor tyrosine kinase and integrin signaling is required for activation of the Ras-Raf-Mek-Erk pathway, which is active in both human and rodent SCs (reviewed in Lee et al., 2004; Monje et al., 2006). Activation of mitogenic receptor tyrosine kinases, in the absence of integrin-dependent adhesion, is coupled only to Ras and Raf and does not lead to Mek and Erk activity. Adhesion of integrins to extracellular matrix activates the Rho family of GTPases and Pak, allowing Pak phosphorylation of c-Raf and Mek. Mek then associates with, and phosphorylates Erk (Del Pozo et al., 2000; Coles and Shaw 2002). One mechanism by which Sch restricts proliferation is by inhibiting Rac-Pak activity in confluent cells (reviewed in Okada et al., 2007). Phosphorylation of Sch downstream of both ErbB and β1 integrin receptors would inactivate this ability and would allow Rac-Pak signaling to couple to Ras-Erk pathways and stimulate proliferation of subconfluent cells.

Consistent with the rapid turnover of focal contacts in subconfluent, motile cells, we find that β1 integrin and ErbB2 protein levels are rapidly modulated by receptor activity. NRG1 has a greater effect on ErbB2 and β1 integrin levels than laminin-1. Whereas laminin-1 stimulates a 30% increase in ErbB2 protein expression over starved SCs, NRG1 promotes a 50% decrease in ErbB2 receptors while increasing β1 integrin levels 2.3 fold over starved SCs. AG825 attenuates the loss of ErbB2 protein in response to NRG1 and inhibits the increase in β1 integrin, confirming that ErbB2 kinase activity modulates the fate of each receptor. In laminin-1 stimulated SCs, AG825 decreases β1 integrin levels, consistent with autocrine stimulation of ErbB2 in SCs. These effects are likely mediated through changes in protein stability and/or degradation, as they occur within 30 minutes of stimulation. Moreover, our results show that each receptor has a different fate after activation, β1 integrins are stabilized following NRG1 stimulation, whereas ErbB2 is degraded. This also implies that ErbB2 dependent inhibition of Pak is transient, and that β1 integrin and Pak dependent phosphorylation of Sch occurs during the time ErbB2 receptor expression on the plasma membrane is low.

Sch is at a critical convergence point for transduction of signals from these receptors, and reveals why loss of this protein in SCs predisposes them to tumor formation. There is evidence that Sch controls endocytosis of ErbB family members, possibly through its interaction with HRS (Scoles et al., 2005; Maitra et al., 2006). Additionally, other paxillin binding proteins regulate vesicle trafficking and receptor degradation (reviewed in Turner, 2000). Of note, human schwannoma cells have increased expression of β1 integrin and activated ErbB2, Rac and Pak (Hansen and Linthicum, 2004; Kaempchen et al. 2003; Utermark et al., 2003). Loss of Sch expression in SCs could allow unrestricted autocrine stimulation of ErbB2/ErbB3, resulting in increased β1 integrin levels and prolonged activation of PKA, Rac-Pak, Ras-Erk and PI3K/AKT pathways. Activation of these signaling cascades would stimulate a slow, but continuous proliferation of SCs, characteristic of schwannoma growth in individuals with NF2.

In summary, we have shown that activation of ErbB2/ErbB3 and β1 integrin receptors promotes phosphorylation of Sch through distinct PKA- and Pak-dependent pathways. In vivo, these signaling cascades would cooperate to promote SC proliferation in response to axonal NRG and basal lamina adhesion. In its phosphorylated state, Sch would also permit Rac-Pak dependent changes in the actin cytoskeleton associated with extension of processes along axons, a critical function for myelination. Our findings shed light on Sch's function during development and pathogenesis in the peripheral nervous system.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

Adam L, Vadlamudi R, Kondapaka S B, Chernoff J, Mendelsohn J, Kumar R. (1998). Heregulin regulates cytoskeletal reorganization and cell migration through the p21-activated kinase-1 via phosphatidylinositol-3 kinase. *J Biol Chem* 273: 2823.

Alfthan K, Heiska L, Gronholm M, Renkema G H, Carpen O. (2004). Cyclic AMP-dependent protein kinase phosphorylates merlin at serine 518 independently of p21-activated kinase and promotes merlin-ezrin heterodimerization. *J Biol Chem.* 279: 18559-66.

Brown M C, West K A, Turner C E. (2002). Paxillin-dependent paxillin kinase linker and p21-activated kinase localization to focal adhesions involves a multistep activation pathway. *Mol Biol Cell* 13: 1550-65.

Chen L M, Bailey D, Fernandez-Valle C. (2000). Association of beta 1 integrin with focal adhesion kinase and paxillin in differentiating Schwann cells. *J Neurosci* 20: 3776-84.

Chen Z L, Strickland S. (2003). Laminin gamma1 is critical for Schwann cell differentiation, axon myelination, and regeneration in the peripheral nerve. *J Cell Biol.* 163: 889-99.

Chernousov M A, Carey D J. (2000). Schwann cell extracellular matrix molecules and their receptors. *Histol Histopathol.* 15: 593-601.

Coles L C, Shaw P E. (2002). PAK1 primes MEK1 for phosphorylation by Raf-1 kinase during cross-cascade activation of the ERK pathway. *Oncogene.* 21:2236-44.

Del Pozo M A, Price L S, Alderson N B, Ren X-D, Schwartz M A. (2000). Adhesion to the extracellular matrix regulates the coupling of the small GTPase Rac to its effector PAK. *EMBO J* 19: 2008-2014.

Dupovy P, Svizenska I, Jancalek R, Klusakova I. Houstava L, Haninec P, et al. (1999). Immunohistochemical localization of laminin-1 in the acellular nerve grafts is associated with migrating Schwann cells which display corresponding integrin receptors. *Gen Physiol Biophys.* 18 63-5.

Fernandez-Valle C, Gwynn L, Wood P M, Carbonetto S, Bunge M B. (1994). Anti-beta 1 integrin antibody inhibits Schwann cell myelination. *J Neurobiol.* 25: 1207-26.

Fernandez-Valle C, Tang Y, Ricard J, Rodenas-Ruano A, Taylor A, Hackler E, et al. (2002). Paxillin binds schwannomin and regulates its density-dependent localization and effect on cell morphology. *Nat Genet* 31: 354-62.

Garratt A N, Britsch S, Birchmeier C. (2000). Neuregulin, a factor with many functions in the life of a Schwann cell. *Bioessays* 22: 987-96.

Hansen M R, Linthicum F H. (2004). Expression of neuregulin and activation of erbB receptors in vestibular schwannomas: possible autocrine loop stimulation. *Otol Neurotol* 25: 155-9.

Howe A K, Juliano R L. (2000). Regulation of anchorage-dependent signal transduction by protein kinase A and p21-activated kinase. *Nat Cell Biol* 2: 593-600.

James M F, Manchanda N, Gonzalez-Agosti C, Hartwig J H, Ramesh V. (2001). The neurofibromatosis 2 protein product merlin selectively binds F-actin but not G-actin, and stabilizes the filaments through lateral association. *Biochem J.* 356: 377-86.

Kaempchen K, Mielke K, Utermark T, Langmesser S, Hanemann C O. (2003). Upregulation of the Rac1/JNK signaling pathway in primary human schwannoma cells. *Hum Mol Genet.* 12: 1211-21.

Kim H A, DeClue J E, Ratner N. (1997). cAMP-dependent protein kinase A is required for Schwann cell growth: interactions between the cAMP and Neuregulin/tyrosine kinase pathways. *J Neurosci Res.* 49: 236-47.

Kissil J L, Johnson K C, Eckman M S, Jacks T. (2002). Merlin phosphorylation by p21-activated kinase 2 and effects of phosphorylation on merlin localization. *J Biol Chem* 277: 10394-9.

Lee J W, Juliano R L. (2004). Mitogenic signal transduction by integrin- and growth factor receptor-mediated pathways. *Mol Cells* 30: 188-202.

Lotti L V, Di Lazzaro, Zompetta C, Frati L, Torrisi M R. (1992). Surface distribution and internalization of erbB-2 proteins. *Exp Cell Res* 202: 274-80.

Maitra S, Kulikauskas R M, Gavilan H, Fehon R G. (2006). The tumor suppressors Merlin and Expanded function cooperatively to modulate receptor endocytosis and signaling. *Curr Biol.* 16: 702-9.

McClatchey A I, Giovannini M. (2005). Membrane organization and tumorigenesis—the NF2 tumor suppressor, merlin. *Genes Dev* 19: 2265-77.

Milner R, Wilby M, Nishimura S, Boylen K, EdwardsG, Fawcett J, et al. (1997). Division of labor of Schwann cell integrins during migration on peripheral nerve extracellular matrix ligands. *Dev Biol.* 185: 215-28.

Monje P V, Bunge M, Wood P M. (2006). Cyclic AMP synergistically enhances Neuregulin-dependent ERK and Akt activation and cell cycle progression in Schwann cells. *Glia* 3: 649-59.

Osherov N, Gazit A, Gilon C, Levitzki A. (1993). Selective inhibition of the epidermal growth factor and HER2/neu receptors by tyrphostins. *J Biol Chem.* 268: 11134-42.

Rong R, Surace E I, Haipek C A, Gutmann D H, Ye K. (2004) Serine 518 phosphorylation modulates merlin intramolecular association and binding to critical effectors important for NF2 growth suppression. *Oncogene* 23: 8447-54.

Rosenbaum C, Karyala S, Marchionni M A, Kim H A, Krasnoselsky A L, Happel B, et al. (1997). Schwann cells express NDF and SMDF/n-ARIA mRNAs, secrete neuregulin, and show constitutive activation of erbB3 receptors: evidence for a neuregulin autocrine loop. *Exp Neurol.* 148: 604-15.

Rouleau G A, Merel P, Lutchman M, Sanson M, Zucman J, Marineau C, et al. (1993). Alteration in a new gene encoding a putative membrane-organizing protein causes neurofibromatosis type 2. *Nature* 363: 515-21.

Scoles D R, Qin Y, Nguyen V, Gutmann D H, Pulst S M. (2005). HRS inhibits EGF receptor signaling in the RT4 rat schwannoma cell line. *Biochem Biophys Res Commun.* 335: 385-92.

Shaw R J, Paez J G, Curto M, Yaktine A, Pruitt W M, Saotome I et al. (2001). The Nf2 tumor suppressor, merlin, functions in Rac-dependent signaling. *Dev Cell* 1: 63-72.

Taylor A R, Geden S E. Fernandez-Valle C. (2003). Formation of a beta 1 integrin signaling complex in Schwann cells is independent of rho. *Glia* 41: 94-104.

Thaxton C, Lopera J, Bott M, Baldwin M E, Kalidas P, Fernandez-Valle C. (2007). Phosphorylation of the NF2 tumor suppressor in Schwann cells is mediated by Cdc42-Pak and requires paxillin binding. *Mol Cell Neurosci* 34: 231-42.

Trofatter J A, MacCollin M M, Rutter J L, Murrell J R, Duyao M P, Parry D M, et al. (1993). A novel moesin-, ezrin-, radixin-like gene is a candidate for the neurofibromatosis 2 tumor suppressor. *Cell* 72: 791-800.

Turner C E. (2000). Paxillin interactions. J Cell Sci. 113: 4139-40.

Utermark T, Kaempchen K, Hanemann C O. (2003). Pathological adhesion of primary human schwannoma cells is dependent on altered expression of integrins. *Brain Pathol* 13: 352-63.

Xiao G H, Beeser A, Chernoff J, Testa J R. (2002). p21-activated kinase links Rac/Cdc42 signaling to merlin. *J Biol Chem* 277: 883-6.

Yang D, Beirman J, Tarumi Y S, Zhong Y P, Rangwala R, Proctor T M et al. (2005). Coordinate control of axon defasiculation and myelination by laminin-2 and laminin-8. *J Cell Biol* 168:655-66.

That which is claimed:

1. A method of circumventing a lack of neurofibromatosis type 2 tumor suppressor activity in Schwann cells, the method comprising:
    contacting Schwann cells lacking neurofibromatosis type 2 suppressor activity with an effective amount of tyrphostin AG825 that inhibits normal function of a receptor selected from the group consisting of ErbB2, ErbB3, β1 integrins and combinations thereof;
    wherein the contacting prevents the cells from receiving a growth signal normally inhibited by a neurofibromatosis type 2 tumor suppressor, and
    wherein the Schwann cells comprise a mutated Schwannomin protein that causes the Schwann cells to lack neurofibromatosis type 2 suppressor activity.

2. A method of preventing a Schwann cell from forming a tumor associated with neurofibromatosis type 2, the method comprising:
    contacting a Schwann cell lacking neurofibromatosis type 2 suppressor activity with an amount of tyrphostin AG825 sufficient to inhibit a receptor selected from the group consisting of ErbB2, ErbB3, β1 integrins and combinations thereof, wherein the contacting prevents the cell from receiving a growth signal normally inhibited by a neurofibromatosis type 2 tumor suppressor, and
    wherein the Schwann cells comprise a mutated Schwannomin protein that causes the Schwann cells to lack neurofibromatosis type 2 suppressor activity.

* * * * *